(12) United States Patent
Ponzer et al.

(10) Patent No.: US 10,172,630 B2
(45) Date of Patent: Jan. 8, 2019

(54) DRILL GUIDE WITH ADJUSTABLE STOP

(71) Applicant: Medos International Sarl, Le Locle (CH)

(72) Inventors: Rainer Ponzer, Himmerlried (CH); Enda Minnock, Liestal (CH); Peter Senn, Waldenburg (CH)

(73) Assignee: Medos International Sarl, Le Locle (CH)

( * ) Notice: Subject to any disclaimer, the term of this patent is extended or adjusted under 35 U.S.C. 154(b) by 229 days.

(21) Appl. No.: 15/159,041

(22) Filed: May 19, 2016

(65) Prior Publication Data

US 2017/0333056 A1 Nov. 23, 2017

(51) Int. Cl.
*A61B 17/17* (2006.01)
*F16G 11/12* (2006.01)
*A61B 17/00* (2006.01)
*A61B 90/00* (2016.01)

(52) U.S. Cl.
CPC .......... *A61B 17/17* (2013.01); *A61B 17/1728* (2013.01); *F16G 11/12* (2013.01); *A61B 17/1757* (2013.01); *A61B 2017/0042* (2013.01); *A61B 2017/0046* (2013.01); *A61B 2017/00407* (2013.01); *A61B 2017/00433* (2013.01); *A61B 2090/062* (2016.02)

(58) Field of Classification Search
CPC ... A61B 17/17; A61B 17/1728; B05C 17/012; B05C 17/0123; F16G 11/12; F16H 2059/047; F16H 63/38; G05G 2700/06; G05G 2700/08; G05G 5/06; G05G 5/24; G05G 7/08
See application file for complete search history.

(56) References Cited

U.S. PATENT DOCUMENTS

| | | | |
|---|---|---|---|
| 322,460 A | * | 7/1885 | Long .................. F16G 11/12 24/134 R |
| 5,330,468 A | | 7/1994 | Burkhart |
| 5,458,602 A | | 10/1995 | Goble et al. |
| 5,501,374 A | * | 3/1996 | Laufer ............... B05C 17/0123 222/391 |
| 5,584,839 A | | 12/1996 | Gieringer |
| 5,658,291 A | | 8/1997 | Techiera |
| 5,716,362 A | | 2/1998 | Treacy |
| 5,746,743 A | | 5/1998 | Greenberg |
| 5,810,828 A | | 9/1998 | Lightman et al. |
| 5,885,298 A | | 3/1999 | Herrington et al. |
| 5,891,150 A | | 4/1999 | Chan |

(Continued)

FOREIGN PATENT DOCUMENTS

GB    308535 A  *  3/1929  ............. F16G 11/12

*Primary Examiner* — Larry E Waggle, Jr.
(74) *Attorney, Agent, or Firm* — Nutter McClennen & Fish LLP

(57) ABSTRACT

Drill guides and related methods are disclosed herein, e.g., for use in surgical procedures. In some embodiments, a drill guide can include an adjustment mechanism that permits one-handed adjustment of the guide depth and does not require that the drill guide be removed from the patient or that the drill be removed from the drill guide when making an adjustment. The adjustment mechanism can include a trigger that moves first and second detents into and out of engagement with a guide stem to allow step-wise adjustment of the guide depth.

23 Claims, 11 Drawing Sheets

(56) References Cited

U.S. PATENT DOCUMENTS

| | | |
|---|---|---|
| 6,210,415 B1 * | 4/2001 | Bester .............. A61B 17/1714 606/96 |
| 6,716,215 B1 | 4/2004 | David et al. |
| 6,866,667 B2 | 3/2005 | Wood et al. |
| 7,060,068 B2 | 6/2006 | Tromanhauser et al. |
| 7,131,974 B2 | 11/2006 | Keyer et al. |
| 7,316,689 B2 * | 1/2008 | Lieberman ....... A61B 17/00234 606/93 |
| 7,357,804 B2 | 4/2008 | Binder, Jr. et al. |
| 7,442,197 B2 * | 10/2008 | Abdelgany ............ A61B 17/17 606/96 |
| 7,575,579 B2 | 8/2009 | Taras et al. |
| 8,066,710 B2 | 11/2011 | Estes et al. |
| 8,277,455 B2 | 10/2012 | Couture et al. |
| 8,361,079 B2 | 1/2013 | Pandya |
| 9,801,641 B2 * | 10/2017 | Keiser ................... A61B 17/17 |
| 2003/0233098 A1 | 12/2003 | Markworth |
| 2007/0118135 A1 | 5/2007 | Mansmann |
| 2010/0234850 A1 | 9/2010 | Dees, Jr. et al. |
| 2012/0123417 A1 | 5/2012 | Smith |
| 2013/0190765 A1 | 7/2013 | Harris et al. |

* cited by examiner

DRILL GUIDE WITH ADJUSTABLE STOP

FIELD

Drill guides and related methods are disclosed herein, e.g., for use in surgical procedures.

BACKGROUND

There are a number of surgical procedures in which it is necessary or desirable to drill a hole. For example, holes are often drilled in bone using a rotary drill bit to prepare the bone to receive a screw or other bone anchor. A number of drill guides have been developed to guide the drill bit along the proper axis, and/or to set the depth to which the drill bit penetrates the bone. Conventional drill guides generally include a handle having an adjustable length sleeve attached thereto. When used in conjunction with a drill bit having a fixed stop, the length of the sleeve can control the depth to which the drill penetrates the bone (and the depth of the consequent hole).

Conventional drill guides often require two hands to adjust the guide depth, which can be cumbersome and time-consuming for the user. In addition, this can undesirably require that the user remove and set aside the drill while the guide is adjusted, and/or that the user remove the guide from the patient during adjustment. Some conventional drill guides may also be susceptible to inadvertent adjustment of the guide depth while drilling.

There is a continual need for improved drill guides and related methods.

SUMMARY

Drill guides and related methods are disclosed herein, e.g., for use in surgical procedures. In some embodiments, a drill guide can include an adjustment mechanism that permits one-handed adjustment of the guide depth and does not require that the drill guide be removed from the patient or that the drill be removed from the drill guide when making an adjustment. The adjustment mechanism can include a trigger that moves first and second detents into and out of engagement with a guide stem to allow step-wise adjustment of the guide depth.

In some embodiments, surgical guide device includes a handle having a proximal end and a distal end; a sleeve at the distal end of the handle having a lumen extending therethrough; a stem telescopically received in the lumen of the sleeve, the stem being longitudinally translatable with respect to the sleeve to set an effective length of the guide device; and an adjustment mechanism being selectively engaged with the stem to advance or retract the stem with respect to the sleeve.

The adjustment mechanism can include a positioning detent and a mover detent. The positioning detent and the mover detent can be selectively engaged with the stem to advance or retract the stem with respect to the sleeve. The adjustment mechanism can include a trigger pivotally mounted to the handle. The trigger can be rotatable with respect to the handle between a first position in which the positioning detent is engaged with the stem and the mover detent is disengaged from the stem and a second position in which the positioning detent is disengaged from the stem and the mover detent is engaged with the stem. Movement of the trigger from the first position to the second position can advance the stem with respect to the sleeve by a half step and movement of the trigger from the second position back to the first position advances the stem with respect to the sleeve by another half step.

In some embodiments, there is no point at which both the positioning detent and the mover detent are disengaged from the stem during movement of the trigger between the first and second positions. Movement of the trigger from the first position to the second position can cause a ramped surface of the mover detent to engage a first ramped surface of the stem to advance the stem with respect to the sleeve; and movement of the trigger from the second position back to the first position can cause a ramped surface of the positioning detent to engage a second ramped surface of the stem to further advance the stem with respect to the sleeve. When the trigger is in the first position, the positioning detent can prevent distal advancement of the stem with respect to the sleeve. The trigger can be biased towards the first position.

The positioning detent can include an engagement surface that extends substantially perpendicular to the stem. The engagement surface of the positioning detent can engage an engagement surface of the stem when the trigger is in the first position. The engagement surface of the stem can extend substantially perpendicular to the stem. The positioning detent and the mover detent can be slidably mounted within respective tracks formed in the handle. The stem can include a plurality of teeth configured to be selectively engaged by the positioning detent and the mover detent. The device can additionally include a release mechanism configured to disengage the positioning detent from the stem without engaging the mover detent with the stem, such that the stem is free to translate longitudinally with respect to the sleeve.

In some embodiments, a method of forming a hole in a bone surface includes positioning a drill guide with respect to the bone surface, the drill guide having a handle, a sleeve, and a stem slidably mounted in the sleeve; adjusting a depth setting of the drill guide by pivoting a trigger mounted to the handle in a first direction, thereby advancing the stem longitudinally with respect to the sleeve a first distance; pivoting the trigger in a second direction opposite to the first direction, thereby further advancing the stem with respect to the sleeve a second distance; and advancing a drill bit through the drill guide to form a hole in the bone surface, the drill guide limiting the maximum penetration depth of the drill bit into the bone surface.

Pivoting the trigger in the first direction can engage a mover detent with the stem and can disengage a positioning detent from the stem, thereby advancing the stem longitudinally with respect to the sleeve the first distance. Pivoting the trigger in the second direction can disengage the mover detent from the stem and can engage the positioning detent with the stem, thereby further advancing the stem with respect to the sleeve the second distance. At least one of the positioning detent and the mover detent can be engaged with the stem at all times during said adjustment of the depth setting. Movement of the trigger in the first direction can cause a ramped surface of the mover detent to engage a first ramped surface of the stem to advance the stem with respect to the sleeve; and movement of the trigger in the second direction can cause a ramped surface of the positioning detent to engage a second ramped surface of the stem to further advance the stem with respect to the sleeve. Engaging and disengaging the positioning detent and the mover detent can include sliding the positioning detent and the mover detent in respective tracks formed in the handle. The method can include disengaging both the positioning detent and the mover detent from the stem such that the stem is free to translate longitudinally with respect to the sleeve.

BRIEF DESCRIPTION OF THE DRAWINGS

The following detailed description is provided in conjunction with the accompanying drawings, in which.

DETAILED DESCRIPTION

Figure 1:
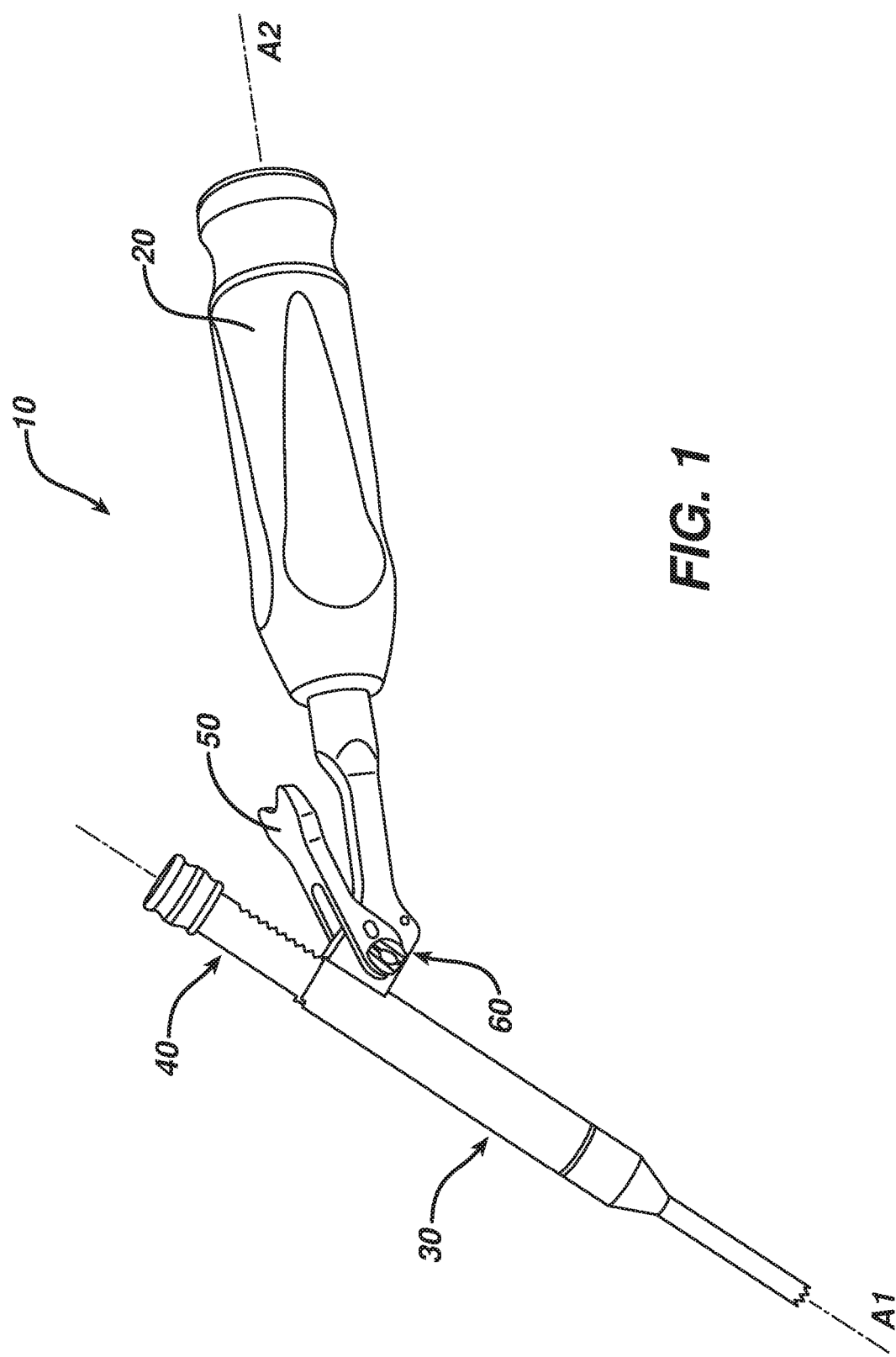
FIG. 1 is a perspective view of a drill guide.
Figure 2:
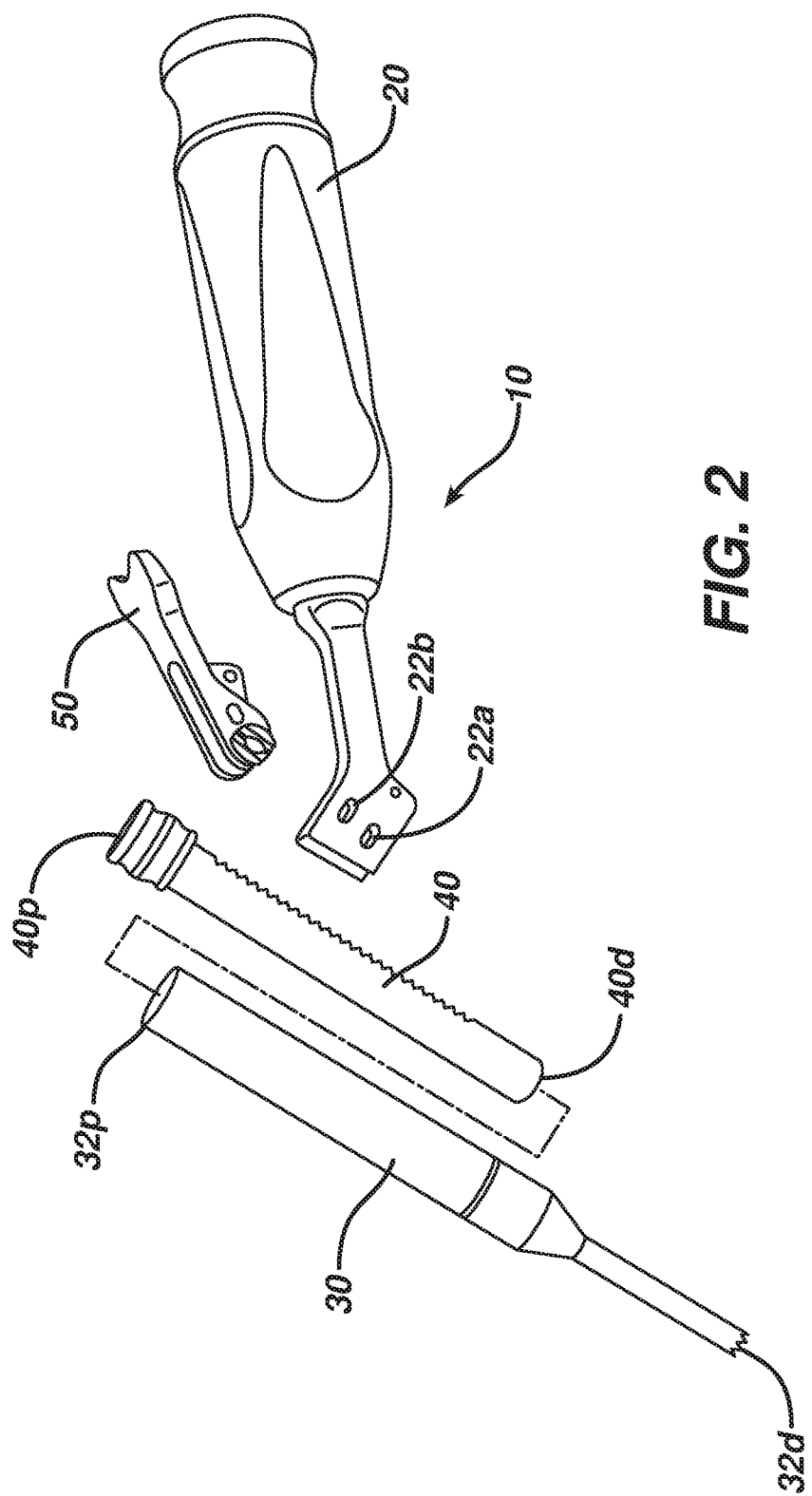
FIG. 2 is an exploded view of the drill guide of FIG. 1.
Figure 3:
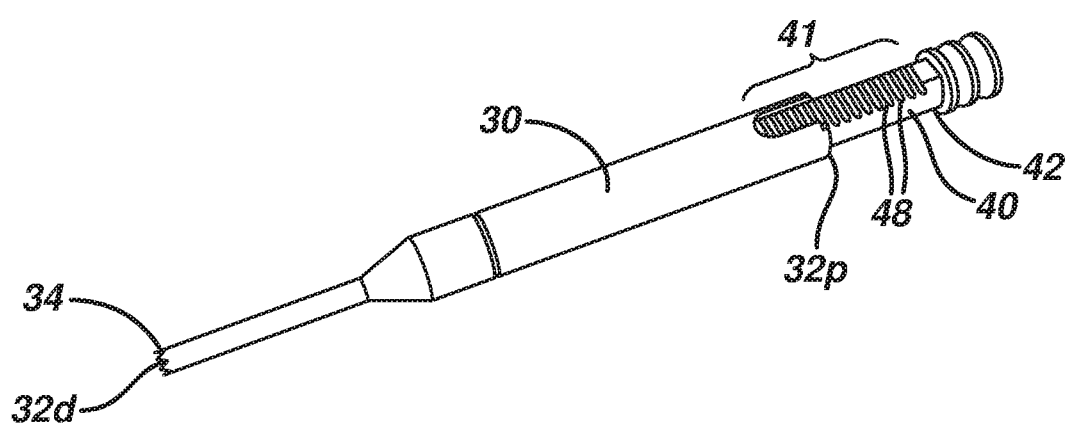
FIG. 3 is a perspective view of a guide sleeve and guide stem of the drill guide of FIG. 1.

Drill guides and related methods are disclosed herein, e.g., for use in surgical procedures. In some embodiments, a drill guide can include an adjustment mechanism that permits one-handed adjustment of the guide depth and does not require that the drill guide be removed from the patient or that the drill be removed from the drill guide when making an adjustment. The adjustment mechanism can include a trigger that moves first and second detents into and out of engagement with a guide stem to allow step-wise adjustment of the guide depth.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments. The features illustrated or described in connection with one exemplary embodiment may be combined with the features of other embodiments.

FIGS. 1-8 illustrate an exemplary embodiment of a drill guide 10. As shown, the drill guide 10 can include a handle 20, a guide sleeve 30, a stem 40, and an adjustment mechanism 60 that includes a trigger 50. In use, the adjustment mechanism 60 can be used to adjust the relative longitudinal position of the stem 40 with respect to the sleeve 30 and thereby establish a maximum drilling depth. A drill bit can be advanced through the stem 40 and the sleeve 30 and into target tissue disposed adjacent the distal end of the sleeve. As the drill bit is advanced, a stop on the drill bit or on the drill contacts the proximal end of the stem 40 to prevent the drill bit from exceeding the maximum drilling depth.

The handle 20 can be shaped and dimensioned to be ergonomic such that a user may comfortably operate the tool using a single hand during a surgical procedure. For example, the handle 20 can include knurling, grooves, ridges, bumps, serrations, or other surface treatments. The handle 20 can include a rubber, silicone, or other coating to enhance user comfort and grip.

Figure 5:
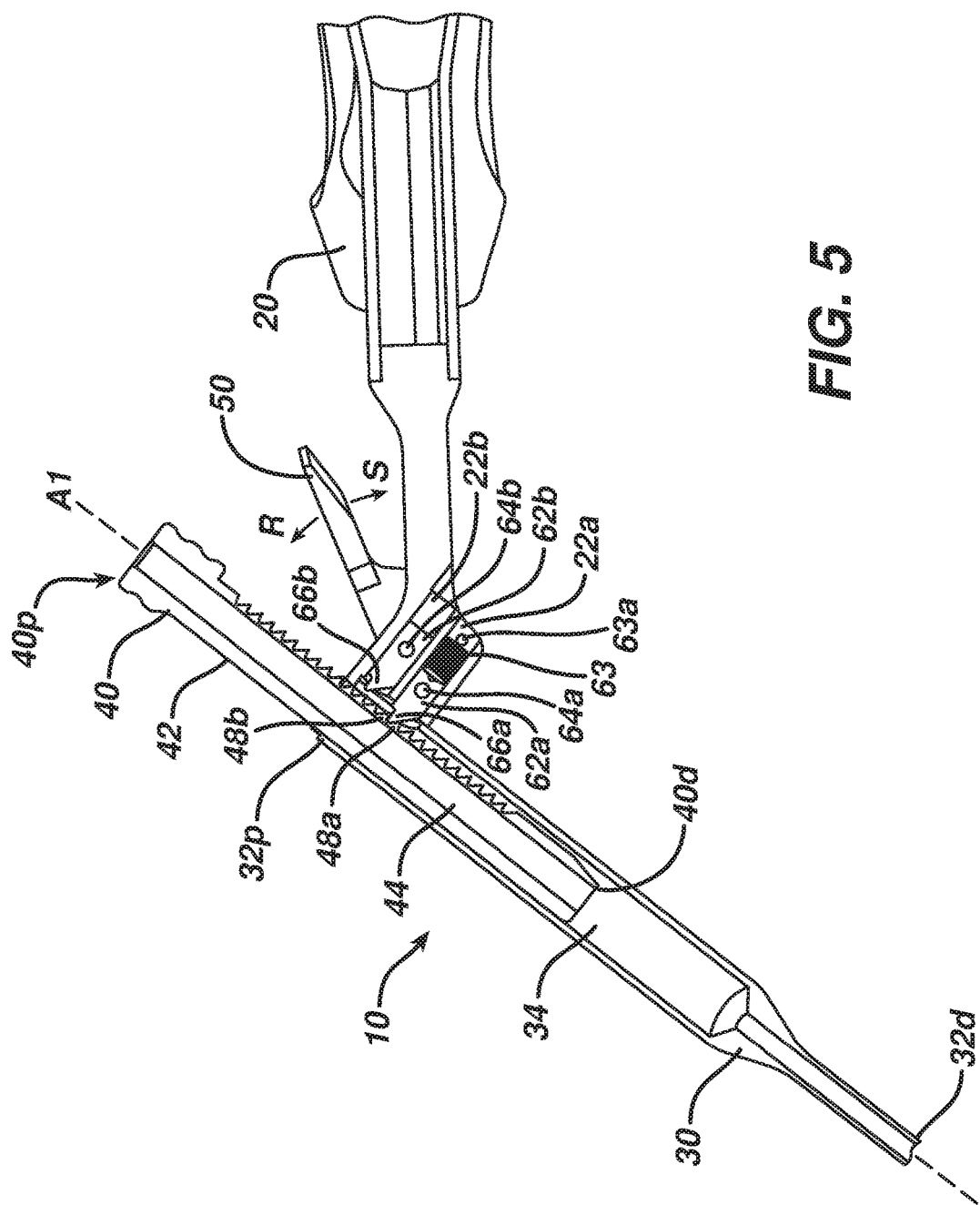
FIG. 5 is a sectional view of the drill guide of FIG. 1.

The drill sleeve 30 can be disposed at a distal end of the handle 20. The sleeve 30 can be a separate component from the handle 20, or can be formed integrally therewith. The sleeve 30 can have a longitudinal axis A1 and the handle 20 can have a longitudinal axis A2. The longitudinal axis A1 of the sleeve 30 can be parallel, perpendicular, or obliquely angled with respect to the longitudinal axis A2 of the handle 20. The angle of the sleeve axis A1 with respect to the handle axis A2 can be fixed, or the angle of the sleeve 30 relative to the handle 20 can be adjustable. The sleeve 30 can define a central lumen 34 extending therethrough along the axis A1. The central lumen 34 can have a substantially circular cross section as shown in FIG. 5, or can have various other cross sectional shapes such as square, rectangular, oval, hexagonal, and so forth. The sleeve 30 can include a proximal end 32p, which can be adjacent to a distal end of the handle 20, and a distal end 32d. The distal end 32d of the sleeve 30 can be conical or can include one or more sharpened tips or protrusions 36 to engage bone and help maintain the sleeve 30 in a fixed position relative to a bone surface.

The stem 40 can be telescopically received within the central lumen 34 of the sleeve 30. The stem 40 can have an outer diameter that is smaller than the diameter of at least a proximal portion of the central lumen 34 such that the stem can move within the central lumen to adjust the drill guide depth. The stem 40 can have an outer surface 42 having a cross section that complements the cross section of the central lumen 34 of the drill sleeve 30. For example, both the outer cross section of the stem 40 and the inner cross section of the central lumen 34 can be circular, square, rectangular, hexagonal, etc. The central lumen 34 and/or the stem 40 can have a flat or other feature such as a pin or track to prevent or limit rotation of the stem relative to the sleeve 30 about the axis A1.

The stem 40 can have a central lumen 44 extending therethrough sized to receive at least a portion of a surgical tool (not shown), such as a drill bit, bone tap, guidewire, needle, etc. While reference is generally made herein to guiding a drill bit, it will be appreciated that the guide 10 can be used with any of a variety of instruments and is not limited to use with drill bits. The central lumen 44 of the stem 40 can have any cross sectional shape to slidably accommodate a surgical tool therein. The stem 40 can have a substantially circular cross section as shown in FIG. 5, or can have various other cross sectional shapes such as square, rectangular, oval, hexagonal, and so forth.

Figure 7:
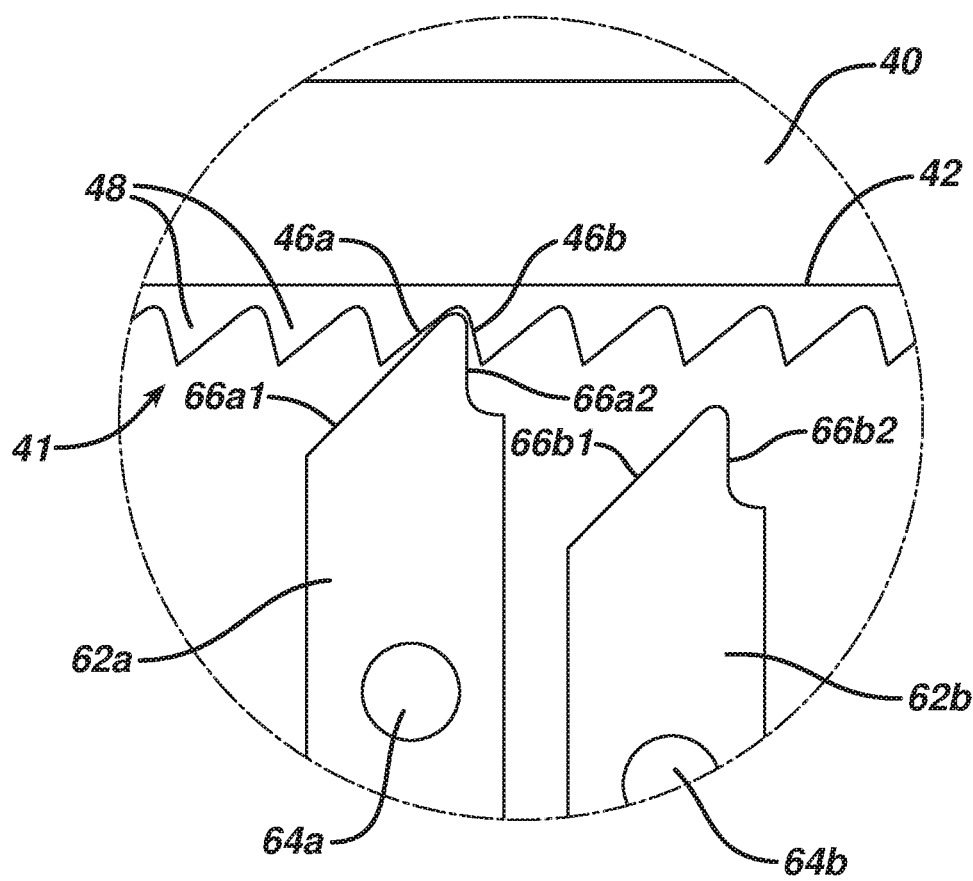
FIG. 7 is a partial view of a rack and detents of the drill guide of FIG. 1.

The outer surface 42 of the stem 40 can include a rack 41. The rack 41 can include a plurality of teeth 48. The series of teeth 48 can extend along an entire length of the stem 40 or along only a portion of the stem's length. The teeth 48 can be disposed at a fixed and predetermined interval (e.g., one tooth every 1 mm, one tooth every 2 mm, etc.) along the length of the stem 40. Each tooth 48 can have a triangular shape. For example, as shown in FIG. 7, each tooth 48 can have a first surface 46a that extends at an oblique angle with respect to the outer surface 42 of the stem 40 and a second surface 46b that extends perpendicular to the outer surface of the stem such that the tooth is in the shape of a right triangle. The first surface 46a can extend at an angle of about 45 degrees from the outer surface 42 of the stem 40. The second surface 46b can extend at an angle of about 85-95 degrees from the outer surface 42 of the stem 40. The second surface 46b can be perpendicular or substantially perpendicular to the outer surface 42.

The stem 40 can include a measurement guide (not shown) printed or otherwise formed on the outer surface 42. The measurement guide can include markings at regular intervals labeled with a depth scale. The depth scale can indicate the adjusted length of the drill guide 10 (e.g., the overall length between the distal end 32d of the sleeve 30 and the proximal end 40p of the stem 40). Alternatively, or in addition, the measurement guide can be calibrated for use with a drill bit having a predetermined length and the depth scale can indicate the maximum penetration depth at the guide's current setting when said drill bit is used. For example, the depth scale can indicate a maximum penetration depth obtained by subtracting the adjusted length of the drill guide 10 from the length of the drill bit. Using this convention, the depth scale can indicate predefined maximum drill penetration depths (e.g., between 10 mm and 50 mm in 2 mm increments, between 10 mm and 60 mm in 2 mm increments, etc.) The scale can be read by the user to determine the maximum drill penetration depth. This can, among other things, allow the user to measure the maximum penetration depth without the use of extra measuring devices, and/or can allow the user to change the maximum penetration depth while the drill guide 10 is still positioned within the incision and/or while the drill bit is positioned within the drill guide.

The adjustment mechanism 60 can be configured to selectively adjust a longitudinal position of the stem 40 with respect to the sleeve 30 (and thus selectively adjust the effective length of the drill guide 10). The adjustment mechanism 60 is shown in greater detail in FIGS. 4-6D. As shown, the adjustment mechanism 60 can include a trigger 50 pivotally mounted to the handle 20, a positioning detent or pin 62a housed within a first track 22a formed in the handle, and a mover detent or pin 62b housed within a second track 22b formed in the handle. The adjustment mechanism 60 can also include a release mechanism 56. The detents 62a, 62b can be coupled to the trigger 50 such that, upon actuation of the trigger 50, the detents 62a, 62b move in generally opposite directions within their respective tracks 22a, 22b to allow for stepwise advancement of the stem 40 relative to the sleeve 30, as described further below. The release mechanism 56 can be actuated to move the positioning detent 62a away from the stem 40 to allow free adjustment of the stem 40 with respect to the sleeve 30.

The trigger 50 can be located at a distal end of the handle 20, adjacent to the drill sleeve 30, where it is easily reachable by a user with the same hand being used to grasp the handle 20. The trigger 50 can be pivotally affixed to the handle 20 with a trigger pin 52. The trigger pin 52 can be rotatably mounted in the handle 20, such that the trigger 50 can pivot relative to the handle 20 about a longitudinal axis of the trigger pin 52. The trigger pin 52 can be coupled to a spring 58 to bias the trigger 50 toward an initial, restricted configuration shown in FIG. 6A. In the illustrated embodiment, the spring 58 is a wire spring having a first end fixedly mounted to the handle 20 and a second end threaded through the trigger pin 52. In other embodiments, the spring 58 can be a coil spring, leaf spring, or any other structure for applying a biasing force.

As noted above, the detents 62a, 62b can be disposed in respective tracks 22a, 22b. The tracks 22a, 22b can be located within the handle 20 such that they are oriented generally perpendicular to the outer surface 42 of the stem 40. The tracks 22a, 22b can be open at their ends opposite the stem 40 allow for easy cleaning and/or sterilization. The trigger 50 can be connected to the detents 62a, 62b via respective guide pins 64a, 64b. The pivoting movement of the trigger 50 can move the detents 62a, 62b into and out of engagement with the rack 41, as discussed below. The guide pins 64a, 64b can be connected to a proximal end of the respective detents 62a, 62b.

The distal end of each of the detents 62a, 62b can include engagement features 66a, 66b defined by first and second surfaces for engaging the teeth 48 of the rack 41.

As shown in FIG. 7, the first surface 66a1, 66b1 of each engagement feature 66a, 66b can extend at an angle of about 45 degrees from the outer surface 42 of the stem 40. The second surface 66a2, 66b2 of each engagement feature 66a, 66b can extend at an angle of about 85-95 degrees from the outer surface 42 of the stem 40. The second surfaces 66a2, 66b2 can be perpendicular or substantially perpendicular to the outer surface 42 and parallel or substantially parallel to the second surface 46b of the teeth 48. Interaction between these opposed surfaces which are substantially parallel to one another and substantially perpendicular to the direction of drill bit advancement can advantageously provide increased resistance to the guide slipping when significant force is applied to the drill bit and/or the drill guide in a distal direction.

Referring again to FIG. 6A, the positioning detent 62a can be biased into engagement with the teeth 48 by a spring 63. The positioning detent 62a can be biased towards the stem 40 to restrict the stem 40 from advancing towards the distal end 32d of the sleeve 30 beyond a desired depth. The spring 63 can be a coil spring which is affixed to the track 22a at pin 63a. Alternatively, the spring 63 can be any spring which provides a biasing force to the positioning detent 62a. As the positioning detent 62a is moved away from engagement with the stem 40, e.g., by movement of the trigger 50, the spring 63 is compressed. Upon release of the trigger 50, the spring 63 can exert a force to advance the positioning detent 62a back towards the stem 40.

Adjustment of the depth of the drill guide 10 is illustrated schematically in FIGS. 6A-6D.

Figure 6A:
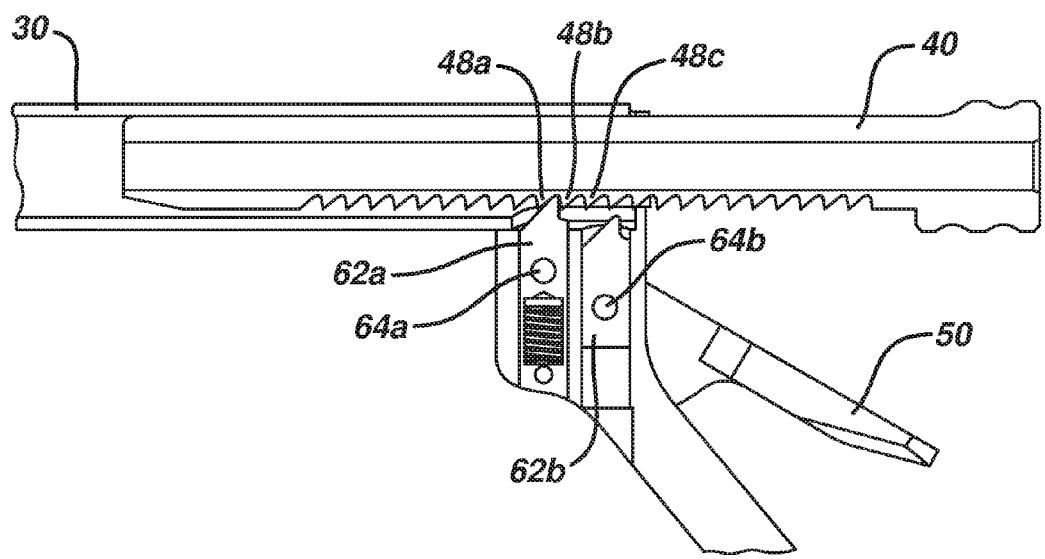
FIG. 6A is a sectional view of the drill guide of FIG. 1 in a first configuration.

As shown in FIG. 6A, the trigger 50 can be positioned in an initial, restricted configuration in which the stem 40 cannot translate longitudinally, in a distal direction, along the axis A1 of the drill sleeve 30. In this configuration, the spring 63 is extended and urges the positioning detent 62a against the rack 41 such that it is located between first and second teeth 48a, 48b. In this configuration, the mover detent 62b is positioned away from the rack 41. Engagement between the second surface 66a2 of the positioning detent 62a and the surface 46b of the tooth 48b prevents distal movement of the stem 40 with respect to the drill sleeve 30.

Figure 6B:
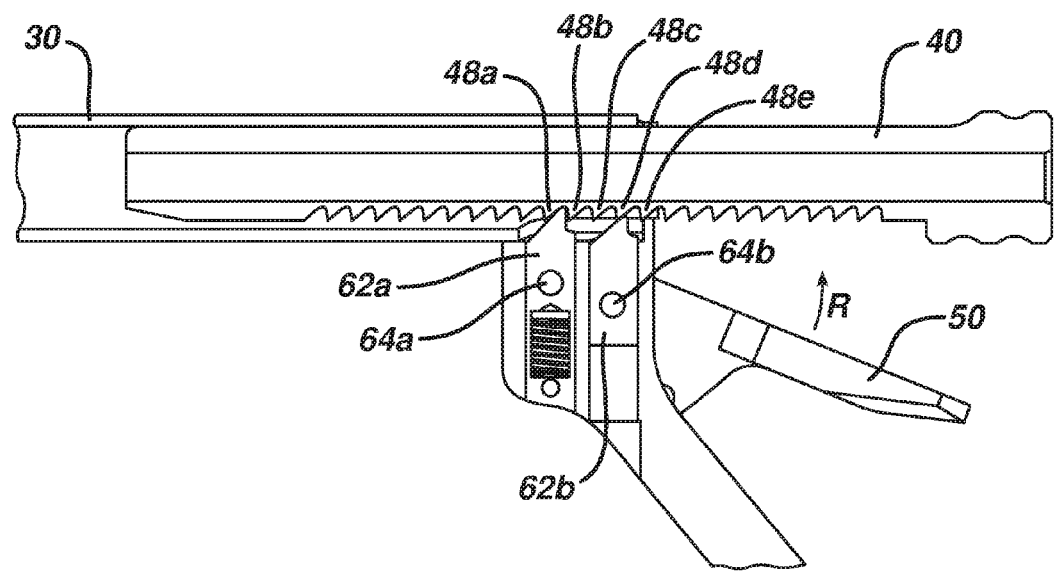
FIG. 6B is a sectional view of the drill guide of FIG. 1 in a second configuration.
Figure 6C:
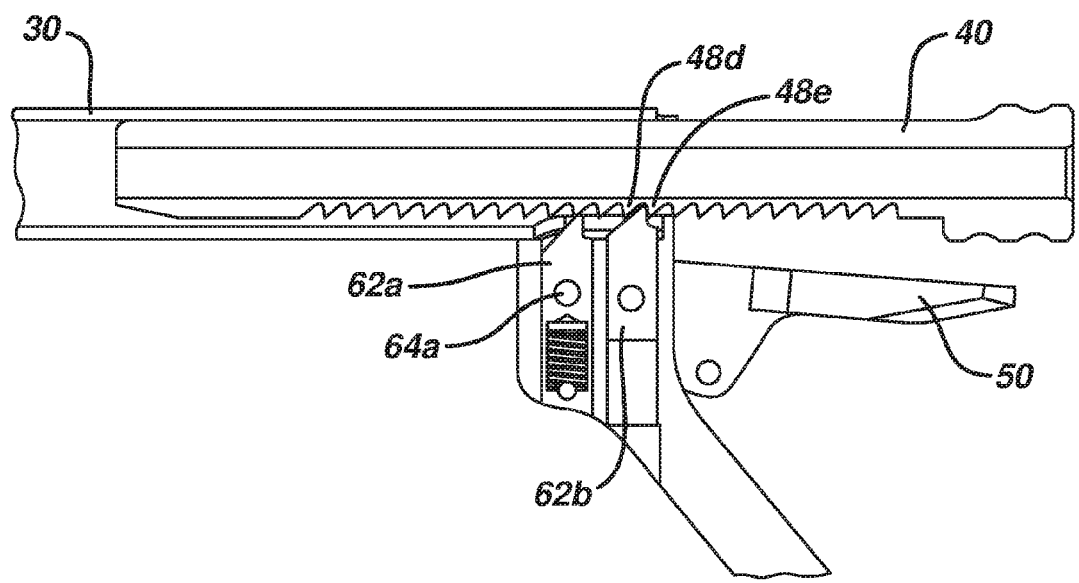
FIG. 6C is a sectional view of the drill guide of FIG. 1 in a third configuration.

To adjust the depth of the drill guide 10, the trigger 50 can be pivoted with respect to the handle 20 in the direction R shown in FIG. 6B. As the trigger 50 pivots in this direction, as shown in FIGS. 6B-6C, it urges the mover detent 62b into engagement with the rack 41 and pulls the positioning detent 62a out of engagement with the rack 41. The mover detent 62b can move into an interference position with the rack 41 before the positioning detent 62a is disengaged, such that the stem 40 is always engaged by at least one detent during the transition. As the ramped end of the mover detent 62b contacts the ramped surface of tooth 48d on the stem 40, the ramping action urges the stem distally by a half step. Further advancement can be prevented by engagement between the second surface 66b2 of the mover detent 62b and the next tooth 48e on the rack 41. When the trigger 50 is released, the bias spring 58 causes the trigger 50 to pivot relative to the handle 20 in the direction S shown in FIG. 6D, returning it to the starting position.

Figure 6D:
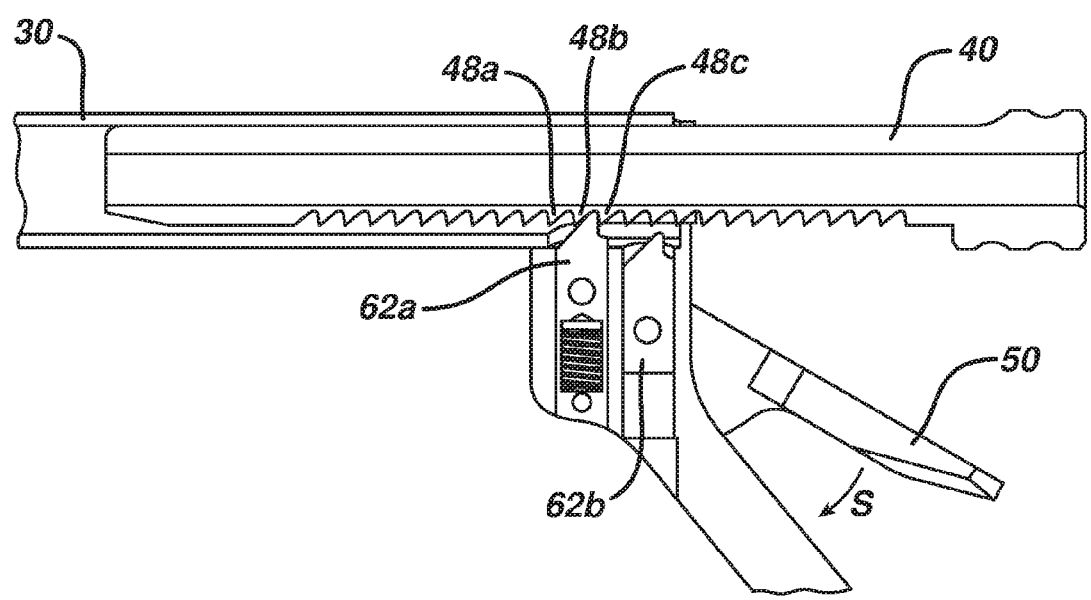
FIG. 6D is a sectional view of the drill guide of FIG. 1 in a fourth configuration.

As the trigger 50 moves towards the starting position, the mover detent 62b is pulled out of engagement with the rack 41 and the positioning detent 62a, under the bias of the spring 63, moves back into engagement with the rack 41, as shown in FIG. 6D. As the positioning detent 62a contacts the rack 41, the ramped end of the positioning detent 62a interacts with the ramped surface 46a of the second tooth 48b to advance the stem 40 distally by another half step. Thus, the two-part movement of pivoting the trigger 50 in the direction R and then pivoting the trigger back in the direction S combines to advance the stem 40 by a complete step (e.g., by one tooth 48). With the trigger 50 returned to the initial position, the positioning detent 62a is located between the next adjacent teeth 48b, 48c and engagement between the second surface 66a2 of the positioning detent 62a and the surface 46b of the next tooth 48c prevents further distal movement of the stem 40 with respect to the drill sleeve 30.

The adjustment mechanism 60 can thus allow for step-wise advancement of the stem 40 relative to the sleeve 30 (e.g., one tooth 48 at a time). This step-wise advancement can advantageously make it difficult or impossible to accidentally advance the stem 40 too far. Also, in some embodiments, the stem 40 is always engaged by at least one of the detents 62a, 62b during step-wise adjustment with the trigger 50, further adding to the safety of the drill guide 10.

The distance that the stem 40 is moved with each complete step can depend on the distance between the teeth 48 of the rack 41 and/or the geometry of the teeth 48 or detents 62a, 62b. In some embodiments, the stem 40 moves 2 mm with each complete advancement step (1 mm with each half step). While the illustrated drill guide 10 shows the trigger 50 advancing the stem 40 in a distal direction, the adjustment mechanism 60 can alternatively be configured to move the stem 40 in a proximal direction. For example, the orientation of the teeth 48 and the detents 62a, 62b can be flipped such that actuation of the adjustment mechanism 60 advances the stem 40 in a proximal direction. The steps as shown in FIGS. 6A-6D can be repeated as many times as required to advance the stem 40 to the desired depth.

Figure 4:
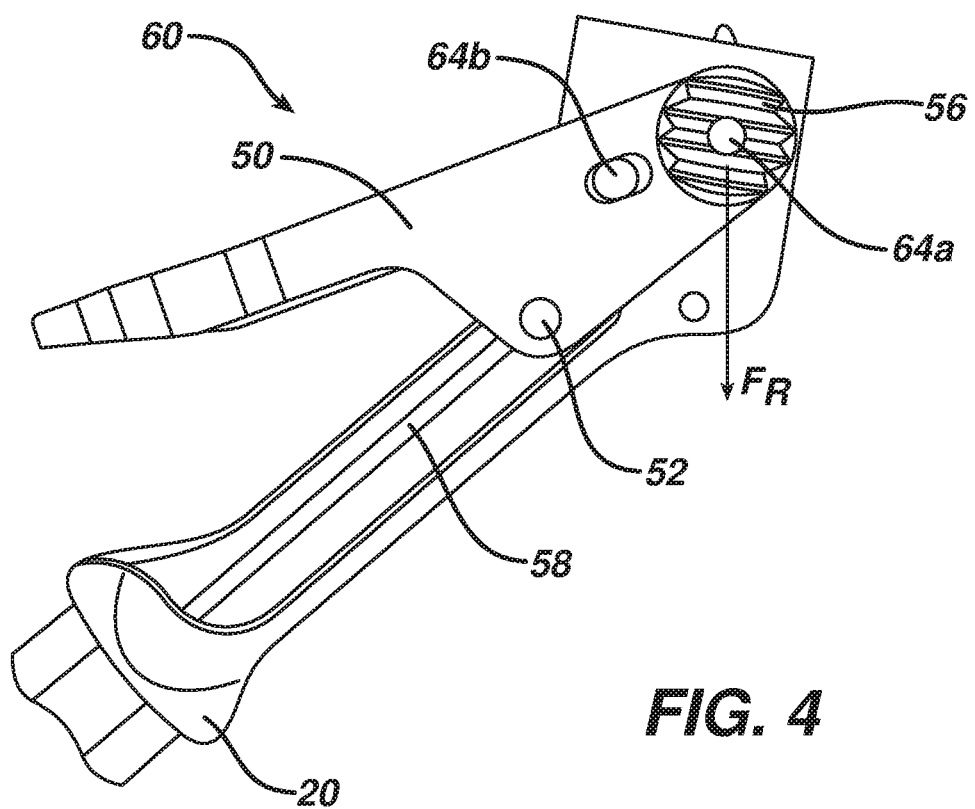
FIG. 4 is a side view of an adjustment mechanism of the drill guide of FIG. 1.
Figure 8:
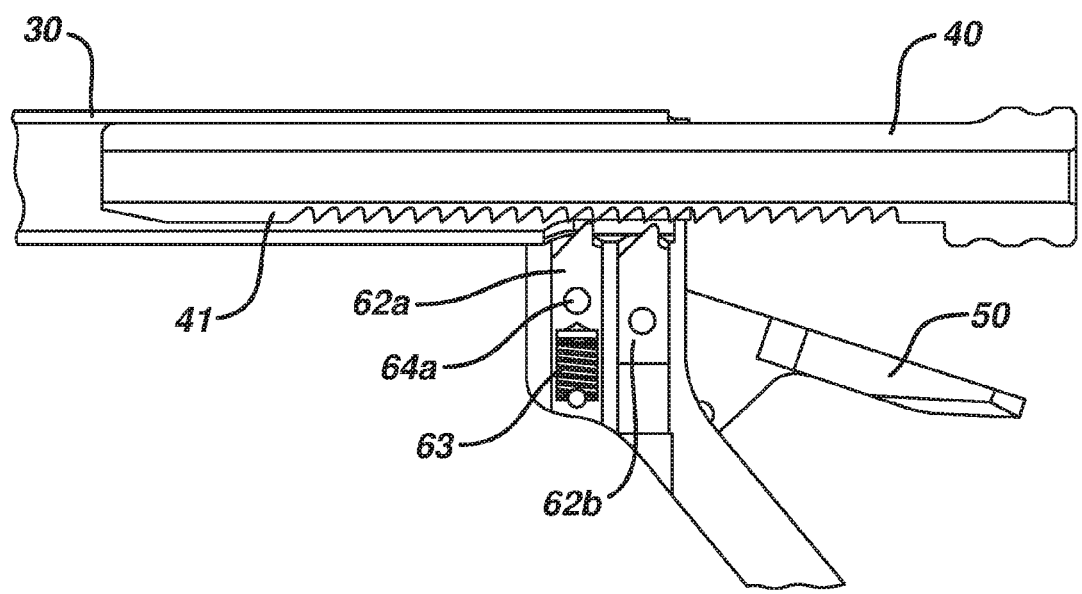
FIG. 8 is a sectional view of the drill guide of FIG. 1 in a released configuration.

As shown in FIGS. 4 and 8, the release mechanism 56 can be actuated to allow free movement of the stem 40 within the sleeve 30, e.g., to remove the stem or to move the stem proximally. The release mechanism 56 can include a grip pad attached to the trigger 50 such applying a force $F_R$ to the grip pad can be effective to pull the trigger 50 back and pull the positioning detent 62a out of engagement with the rack 41. Accordingly, both detents 62a, 62b are disengaged from the rack 41 and the stem 40 is free to translate longitudinally with respect to the sleeve 30, such that the stem can be removed from the sleeve or adjusted proximally or distally to a desired position. Once the force $F_R$ is removed from the release mechanism 56, the spring 63 can force the positioning detent 62a back into engagement with the rack 41, returning the drill guide 10 to the restricted configuration.

The grip pad of the release mechanism 56 can have a knurled or textured face to allow for ease of engagement by the user. The grip pad 56 can be located on a single outer surface of the trigger 50, or the drill guide 10 can include two grip pads, one on either side of the trigger. The release mechanism 56 can be configured to move in a direction parallel to a longitudinal axis of the track 22a in which the positioning detent 62a is housed.

An exemplary method of using the drill guide 10 in a surgical procedure to install a bone anchor is described below. It will be appreciated that the drill guide 10 can be used in any of a variety of other procedures instead or in addition.

The drill guide 10 can be positioned at a target site on the bone surface and at a desired trajectory. In some embodiments, the bone can be a vertebra and the target site can be at a pedicle or lateral mass of the vertebra. The drill guide 10 can be positioned by guiding the sleeve 30 and the stem 40 disposed therein over a guide wire to the target site, using fluoroscopic guidance, using surgical navigation, or various other known techniques. The sharpened distal tip of the sleeve 30 can be docked into the bone surface to help retain the drill guide 10 at the target site.

Before or after positioning the drill guide at the target site, the depth of the drill guide can be adjusted to the desired position. For example, the release mechanism 56 can be actuated to allow free positioning of stem relative to the sleeve, or the trigger 50 can be actuated to adjust the guide depth in a stepwise manner. The user can reference depth markings on the exterior of the drill guide 10 to confirm that the depth is set to the desired amount.

A drill bit can be inserted through the stem 40 and the sleeve 30 of the drill guide 10 and driven into the bone surface to form a bone hole. The user can form a bone hole of the desired depth by simply advancing the drill bit distally until a stop on the drill bit or the drill contacts the proximal end of the drill guide 10 to prevent further insertion.

At any time during the procedure, the user can safely and confidently increase the maximum penetration depth of the drill bit in a stepwise manner by successively actuating the trigger 50. This adjustment can be performed using only a single hand of the user, and does not require that the drill guide 10 be removed from the target site or that the drill bit be removed from the drill guide. The stem 40 and the drill bit can be removed once the bone hole is formed to allow the sleeve 30 to act as a guide for another instrument or implant, or to allow the drill guide 10 to be removed from the surgical site. Once the bone hole is formed, a bone anchor can be advanced into the bone hole and the procedure can be completed using known techniques.

It should be noted that any ordering of method steps expressed or implied in the description above or in the accompanying drawings is not to be construed as limiting the disclosed methods to performing the steps in that order. Rather, the various steps of each of the methods disclosed herein can be performed in any of a variety of sequences. In addition, as the described methods are merely exemplary embodiments, various other methods that include additional steps or include fewer steps are also within the scope of the present disclosure.

The devices disclosed herein and the various component parts thereof can be constructed from any of a variety of known materials. Exemplary materials include those which are suitable for use in surgical applications, including metals such as stainless steel, polymers such as PEEK, ceramics, carbon fiber, and so forth. The various components of the devices disclosed herein can be rigid or flexible. One or more components or portions of the device can be formed from a radiopaque material to facilitate visualization under fluoroscopy and other imaging techniques, or from a radiolucent material so as not to interfere with visualization of other structures. Exemplary radiolucent materials include carbon fiber and high-strength polymers.

The devices and methods disclosed herein can be used in minimally-invasive surgery and/or open surgery. While the devices and methods disclosed herein are generally described in the context spinal surgery, it will be appreciated that the devices and methods disclosed herein can be used in any of a variety of surgeries performed on humans or animals, and/or in fields unrelated to surgery.

Although specific embodiments have been described, it should be understood that numerous changes may be made within the spirit and scope of the concepts described.

The invention claimed is:

1. A surgical guide device comprising:
   a handle having a proximal end and a distal end;
   a sleeve at the distal end of the handle having a lumen extending therethrough;
   a stem telescopically received in the lumen of the sleeve, the stem being longitudinally translatable with respect to the sleeve to set an effective length of the guide device; and
   a trigger movable between a first position and a second position, wherein movement of the trigger from the first position to the second position advances or retracts the stem with respect to the sleeve in a first direction and movement of the trigger from the second position back to the first position further advances or retracts the stem with respect to the sleeve in the first direction.

2. The device of claim 1, further comprising a positioning detent and a mover detent, the positioning detent and the mover detent being selectively engaged with the stem to advance or retract the stem with respect to the sleeve.

3. The device of claim 2, wherein the trigger is rotatable with respect to the handle between the first position in which the positioning detent is engaged with the stem and the mover detent is disengaged from the stem and the second position in which the positioning detent is disengaged from the stem and the mover detent is engaged with the stem.

4. The device of claim 3, wherein movement of the trigger from the first position to the second position advances the stem with respect to the sleeve by a half step in the first direction and movement of the trigger from the second position back to the first position advances the stem with respect to the sleeve by another half step in the first direction.

5. The device of claim 4, wherein there is no point at which both the positioning detent and the mover detent are disengaged from the stem during movement of the trigger between the first and second positions.

6. The device of claim 3,
   wherein movement of the trigger from the first position to the second position causes a ramped surface of the mover detent to engage a first ramped surface of the stem to advance the stem with respect to the sleeve; and
   wherein movement of the trigger from the second position back to the first position causes a ramped surface of the positioning detent to engage a second ramped surface of the stem to further advance the stem with respect to the sleeve.

7. The device of claim 3, wherein, when the trigger is in the first position, the positioning detent prevents distal advancement of the stem with respect to the sleeve.

8. The device of claim 3, wherein the trigger is biased towards the first position.

9. The device of claim 2, wherein the positioning detent includes an engagement surface that extends substantially perpendicular to the stem.

10. The device of claim 9, wherein the engagement surface of the positioning detent engages an engagement surface of the stem when the trigger is in the first position, the engagement surface of the stem extending substantially perpendicular to the stem.

11. The device of claim 2, wherein the positioning detent and the mover detent are slidably mounted within respective tracks formed in the handle.

12. The device of claim 2, wherein the stem includes a plurality of teeth configured to be selectively engaged by the positioning detent and the mover detent.

13. The device of claim 2, further comprising a release mechanism configured to disengage the positioning detent from the stem without engaging the mover detent with the stem, such that the stem is free to translate longitudinally with respect to the sleeve.

14. The device of claim 1, wherein the trigger is pivotally mounted to the handle.

15. A method of forming a hole in a bone surface, comprising:
   positioning a drill guide with respect to the bone surface, the drill guide having a handle, a sleeve, and a stem slidably mounted in the sleeve;
   adjusting a depth setting of the drill guide by:
      pivoting a trigger mounted to the handle in a first direction, thereby advancing the stem longitudinally with respect to the sleeve a first distance;
      pivoting the trigger in a second direction opposite to the first direction, thereby further advancing the stem with respect to the sleeve a second distance; and
   advancing a drill bit through the drill guide to form the hole in the bone surface, the drill guide limiting a maximum penetration depth of the drill bit into the bone surface.

16. The method of claim 15,
   wherein pivoting the trigger in the first direction engages a mover detent with the stem and disengages a positioning detent from the stem, thereby advancing the stem longitudinally with respect to the sleeve the first distance; and
   wherein pivoting the trigger in the second direction disengages the mover detent from the stem and engages the positioning detent with the stem, thereby further advancing the stem with respect to the sleeve the second distance.

17. The method of claim 16, wherein at least one of the positioning detent and the mover detent is engaged with the stem at all times during said adjustment of the depth setting.

18. The method of claim 16,
   wherein movement of the trigger in the first direction causes a ramped surface of the mover detent to engage a first ramped surface of the stem to advance the stem with respect to the sleeve; and
   wherein movement of the trigger in the second direction causes a ramped surface of the positioning detent to engage a second ramped surface of the stem to further advance the stem with respect to the sleeve.

19. The method of claim 16, wherein engaging and disengaging the positioning detent and the mover detent comprises sliding the positioning detent and the mover detent in respective tracks formed in the handle.

20. The method of claim 16, further comprising disengaging both the positioning detent and the mover detent from the stem such that the stem is free to translate longitudinally with respect to the sleeve.

21. A surgical guide device comprising:
   a handle having a proximal end and a distal end;
   a sleeve at the distal end of the handle having a lumen extending therethrough;

a stem telescopically received in the lumen of the sleeve, the stem being longitudinally translatable with respect to the sleeve to set an effective length of the guide device; and an adjustment mechanism being selectively engaged with the stem to advance or retract the stem with respect to the sleeve, wherein the adjustment mechanism includes a positioning detent and a mover detent, the positioning detent and the mover detent being selectively engaged with the stem to advance or retract the stem with respect to the sleeve, and wherein the positioning detent and the mover detent are slidably mounted within respective tracks formed in the handle.

22. The device of claim 21, wherein the tracks are disposed in the same plane.

23. The device of claim 21, wherein the positioning detent and the mover detent are configured to move in opposite directions within the respective tracks.

\* \* \* \* \*